US006635678B1

(12) United States Patent
Kamm et al.

(10) Patent No.: US 6,635,678 B1
(45) Date of Patent: Oct. 21, 2003

(54) PHARMACEUTICAL COMPOSITION FOR TREATING FECAL INCONTINENCE

(75) Inventors: Michael A. Kamm, London (GB); Robin K. S. Phillips, Northwood (GB)

(73) Assignee: S.L.A. Pharma AG, Liestal (CH)

( * ) Notice: Subject to any disclaimer, the term of this patent is extended or adjusted under 35 U.S.C. 154(b) by 0 days.

(21) Appl. No.: 09/331,163

(22) PCT Filed: Dec. 23, 1997

(86) PCT No.: PCT/GB97/03525
§ 371 (c)(1),
(2), (4) Date: Aug. 24, 1999

(87) PCT Pub. No.: WO98/27971
PCT Pub. Date: Jul. 2, 1998

(30) Foreign Application Priority Data

Dec. 23, 1996 (GB) ............................................. 9626739
Dec. 23, 1996 (GB) ............................................. 9626750
Feb. 18, 1997 (GB) ............................................. 9703309

(51) Int. Cl.$^7$ ..................... A61K 31/135; A61K 31/185
(52) U.S. Cl. ...................................... 514/653; 514/576
(58) Field of Search ................................ 514/653, 576

(56) References Cited

U.S. PATENT DOCUMENTS

| 4,292,300 A | 9/1981 | Byrne et al. .................. 424/19 |
| 5,213,808 A | 5/1993 | Bar-Shalom et al. ....... 424/473 |
| 5,436,009 A | 7/1995 | Jauw et al. ................. 424/436 |

FOREIGN PATENT DOCUMENTS

WO    WO91/00730    1/1991

OTHER PUBLICATIONS

Drug Facts and Comparisons. Aug. 1987. pp. 538–540.*
P. Enck et al., "Die Behandlung der Analinkotinenz", Internist, vol. 34, No. 1, 1993, pp. 51–58.
Burleigh et al., "Neural and Pharmacological Factors Affecting Motility of the Internal Anal Sphincter", Gastroenterology, vol. 84, No. 2, 1983.
Yamamoto et al., "Role of alpha Adrenoceptors in Opossum Internal Anal Sphincter", J. Clin. Invest, vol. 86, No. 2 1990, pp. 424–429.
Hechtmann et al., "Moderation of Anal Sphincter Tone with Nitric Oxide Agonists and Antagonists," Archives of Surgery, vol. 131, No. 7, 1996, pp. 775–778.
Rattan et al., "Role of Nitric Oxide as a Mediator of Internal Anal Sphincter Relaxation", Am. J. Physiol, vol. 262, No. 1, 1992, pp. 107–112.
Gut, 1991, vol. 32, pp. 345–346.
Br. J. Surg., 1992, vol. 79, Aug., pp. 829–832.
Coloproctology and the Pelvic Floor, $2^{nd}$ Edition, 1992, Chapter 3, pp. 37–53.
New England Journal of Medicine, Apr. 1992, pp. 1002–1007.
Gastroenterology in Practice, Summer 1995, pp. 18–21.
Dig. Dis., 1990, vol. 8, pp. 179–188.
Digestive Diseases and Sciences, vol. 38, No. 11, Nov. 1993, pp. 1961–1969.
Br. J. Surg, 1990, vol. 77, Dec., pp. 1342–1344.
Surgery, Mar., 1990, vol. 107, No. 3, pp. 311–315.

* cited by examiner

*Primary Examiner*—Theodore J. Criares
*Assistant Examiner*—Jennifer Kim
(74) *Attorney, Agent, or Firm*—Birch, Stewart, Kolasch & Birch, LLP

(57) ABSTRACT

Fecal incontinence and anal itch can be treated by administration, more particularly by local application to the anus, of an a adrenergic blocker, nitric oxide synthase inhibitor, prostaglandin $F_{2\alpha}$, dopamine, morphine, β-blockers, and 5-Hydroxytryptamine. The patients who benefit most from the invention are those who have a normal or low maximum anal resting pressure and a structurally intact internal anal sphincter muscle, and patients who have had major bowel resection and reanastomisis.

7 Claims, 4 Drawing Sheets

PHARMACEUTICAL COMPOSITION FOR TREATING FECAL INCONTINENCE

This Application is a 371 of PCT/GB97/03525 filed Dec. 23, 1987

This invention relates to the treatment of relief of fecal incontinence and anal itch (pruritis ani), particularly for patients who have had a major bowel resection and reanastomosis.

Anal or fecal incontinence is the inability to voluntarily control the passage of feces or gas through the anus. It may occur either as fecal soiling or as rare episodes of incontinence for gas or watery stools. It is a very distressing condition that can result in self-inflicted social isolation and despair.

Conventional treatments for fecal incontinence include drug therapy to improve stool consistency, such as morphine, loperamide and codeine phosphate to reduce gut motility, and laxatives to soften stools and relieve constipation. Biofeedback training is another treatment which involves muscle strengthening exercises to improve anal canal resting pressure, and squeeze pressure, and to teach symmetry of anal canal function. The most common form of treatment however, is surgical repair, such as the creation of a neo-sphincter which involves grafting on muscle from other parts of the anus, or a colostomy. (Gastroenterology in Practice, Summer 1995, p18–21; Dig Dis 1990; 8:179–188; and The New England Journal of Medicine, April 1992, p1002–1004). In mild cases of anal leakage, the patient will often try and plug the anus with a ball of cotton wall.

In Gut, 1991, 32, p. 345–346 it was reported that two thirds of patients with idiopathic faecal incontinence had a decreased anal resting pressure resulting from an abnormal internal sphincter function. In many incontinent patients, the internal anal sphincter was found to be abnormally thin, while others had an external anal sphincter defect.

It has also been reported that in vitro contractile response of the internal anal sphincter to noradrenaline is decreased in incontinence, (Br. J. Surg. 1992, vol 79, August, p829–832; Digestive Diseases and Sciences, vol 38, no. 11, November 1993, p1961–1969). A further discussion of the innervation and control of the internal anal sphincter and drugs which can increase or decrease the normal anal resting pressure, is discussed in the text book Coloproctology and the Pelvic Floor (Butterworths), second edition, 1992, at chapter 3 p37–53; Automic Control of Internal Anal Sphincter; and Journal of Clinical Investigation 1990, 86: p424–429.

In Surgery 1990; 107: p311–315 sodium valproate was found to be useful in the treatment of minor incontinence after ileoanal anastomosis.

It has now surprisingly been found that fecal incontinence and anal itch can be resolved by treatment with $\alpha$ adrenergic agonists, nitric oxide synthase inhibitors, prostaglandins $F_{2\alpha}$, dopamine, morphine, $\beta$-blockers such as propranolol, and 5—Hydroxytryptamine (5—HT).

This is surprising since it was always thought that once an anal sphincter began functioning abnormally, the patient would require major surgery.

In this way the anal leakage is reduced or eliminated without the patient having to undergo major surgery.

Accordingly in a first aspect of the invention there is provided method for the treatment or prophylaxis of fecal incontinence or anal itch by topical application in and/or around the anal canal of a patient, a therapeutically active amount of a physiologically active agent selected from an $\alpha$ adrenergic agonist, nitric oxide synthase inhibitor, prostaglandin $F_{2\alpha}$, dopamine, morphine, $\beta$-blockers, and 5—Hydroxytryptamine The agents of the invention appear to at least partially treat the incontinence by increasing the resting pressure of the internal anal sphincter.

Preferred agents are al adrenergic agonists, nitric oxide synthase inhibitors, and prostaglandin $F_{2\alpha}$.

Examples of suitable $\alpha_1$ adrenergic agonists are nor—adrenalin, methoxamine, but particularly preferred is phenylephrine.

Examples of suitable $F_{2\alpha}$prostaglandin are dinoprost and carboprost.

Examples of suitable NO synthase inhibitors are $N^G$—monomethyl-L-arginine (L-NMMA), and $N^G$—nitro-L-arginine methyl ester (L-NAME).

The medicament can contain a single active agent or a combination of any of the above active agents.

Nitric Oxide (NO) synthase inhibitors such as LNMMA have previously been suggested for the therapeutic treatment of septic shock.

The prostaglandins, along with thromboxanes and leukotrienes are all derived from 20-carbon polyunsaturated fatty acids an are collectively termed eicosanoids. $F_{2\alpha}$prostaglandins derived in vivo from the endoperoxide prostaglandin $H_2$ which turn derived from leukotrienes. Clinically, $F_{2\alpha}$prostaglandin preparations such as dinoprost and carboprost are used as uterine stimulants in the termination of pregnancy, missed abortion or the induction of labor.

Phenylephrine (an $\alpha_1$ adrenergic agonist) is used as a mydriatic in ophthalmology, and as a decongestant, for example, in cold and flu remedies.

However there has been no suggestion to the iventors knowledge of using any of these active agents to treat fecal incontinence or anal itch.

As used herein "fecal incontinence" includes all types of anal leakage from minor leakage or 'spotting' through moderate leakage, to major instances of faecal incontinence, and includes neurogenic, active, urge and passive incontinence.

More particularly the class of incontinent patients who will benefit most from the present invention are those with idiopathic incontinence and those whose incontinence is at least partly due to a weakness of either the internal or external anal sphincter, especially those with a normal or low maximum anal pressure and a structurally intact internal anal sphincter muscle, such as with an abnormally thin sphincter. However patients with minor structural damage such as a fragmented sphincter would still benefit from the invention. Not only incontinent patients with a damaged or abnormal internal sphincter can be treated, but also patients with a damaged or abnormal external sphincter since the increase in the internal anal resting tone induced by the invention will compensate for a poorly functioning external sphincter.

Another class of patients who particularly benefit from the invention are post-surgical patients who have had major bowel resection and reanastomosis. For example patients with ileoanal pouch (restorative proctocolectomy), coloanal (with or without colonic pouch) anostomosis, lower anterior resection, and colectomy with ileorectal anastomosis.

The damage to the sphincter could be caused by trauma, such as experienced in child birth, surgical operations, or road traffic accidents. Furthermore it is also believed that incontinence caused by primary internal anal degeneration can also be relieved by the invention.

Anal leakage also often leads to pruritis of the anus and therefore by reducing or eliminating the leakage, the pruritis or anal itch is also relieved or prevented.

Furthermore, as a result of the increased anal resting pressure, the patient no longer has the discomfort of distended anal sphincter muscles.

Physiologically acceptable salts of the above active compounds are also within the scope of the invention. Suitable salts include those formed with both organic and inorganic acids, such as those formed from hydrochloric, hydrobromic, sulphuric, citric, tartaric, phosphoric, lactic, pyruvic, acetic, trifluoroacetic, succinic, oxalic, fumaric, maleic, oxaloacetic, methanesulphonic, ethanesulphonic, p-toluenesulphonic, benzenesulphonic and isethionic acids.

By salt we also mean to include any complex or pseudo salt wherein the active agent (such as phenylephrine) is associated with, for example, a derivative to an organic or inorganic acid.

Prodrugs and any other bioprecursor which are converted in vivo to the active agents (such as phenylephrine) are also within the scope of the invention.

A particularly preferred salt of phenylephrine is the hydrochloride salt.

Although the medicament can be administered, for example, orally or intravenously to systemically treat the faecal incontinence, it is preferred that the incontinence is treated by local or topical application of the medicament in and/or around the anal canal of the incontinent patient. Alternatively the agents of the invention can be locally injected directly into the internal anal sphincter. In both locally and systemically acting compositions, at least a pharmacologically acceptable carrier will be present along with the active.

Pharmaceutical compositions adapted for oral administration may be presented as discrete units such as capsules or tablets; powders or granules; solutions or suspensions in aqueous or non-aqueous liquids; edible foams or whips; oil-in-water liquid emulsions or water-in-oil liquid emulsions.

Pharmaceutical composition adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water, immediately prior to use.

Pharmaceutical compositions adapted for topical administration in and/or around the anal canal may be formulated as ointments, creams, suspensions, lotions, powders, solutions, pastes, gels, sprays, foam, oils, suppositories or enemas.

The topical compositions can comprise emulsifiers, preservatives, buffering agents and anti-oxidants. Preferably the compositions also comprise steroids and locally acting anaesthetics.

The dosage of the composition will depend on the severity of the incontinence, the route of administration, the age, weight and condition of the patient being treated. For example a suitable daily dosage of medicament, such as phenylephrine, based on a 70 kg patient with moderate faecal incontinence would be 40 mg/day to 2000 mg/day, such as 40 to 400 mg or 40 to 200 mg/day, preferably at a lower limit of at least 50 mg/day.

For rectally administered topical compositions such as phenylephrine, the percentage of active is preferably at least 5% w/w, more preferably at least 10% w/w, and advantageously up to about 50% w/w of the composition. The dosage of active such as phenylephrine is preferably at least 40 mg per 0.5 ml of composition, more preferably at least 50 mg per 0.5 ml of composition, such as up to about 250 mg/0.5 ml. In fact, early investigations indicate that higher dosages will be more beneficial because of the subnormal sensitivity of the anal sphincter. The total amount of active present in a topical composition (such as a tube) is suitably from 40 to 5000 mg, such as 40 mg to 1000 mg, or 40 to 500 mg of active. The topical composition should be applied 1 to 6 times daily, such as 3 times daily until there is a relief from the incontinence.

The topical composition may comprise skin penetrating agents, particularly the sulphoxides, such as dimethyl sulphoxide (DMSO) preferably at 25% to 50% w/w. Amides, (DMA, DMF) pyrrolidones, organic solvents, laurocaprom (AZONE) and calcium thioglycollate are suitable alternative penetrants. The composition may also optionally contains a polyacrylic acid derivative, more particularly a carbomer. This would both act as a skin hydrating agent to aid penetration of the drug, but also an emulsifying agent. The carbomer will help emulsify the DMSO, thereby mitigating skin irritation and providing enhanced skin hydration. Propylene glycol may also be present in the composition to soften the skin, increase thermodynamic potential and aid skin penetration by the DMSO and thus the drug. The final pH of the composition is advantageously pH 3.5 to 4.5.

The invention will now be described by way of example only with reference to the accompanying drawings in which.

EXAMPLE 1

Protocol

Figure 1:
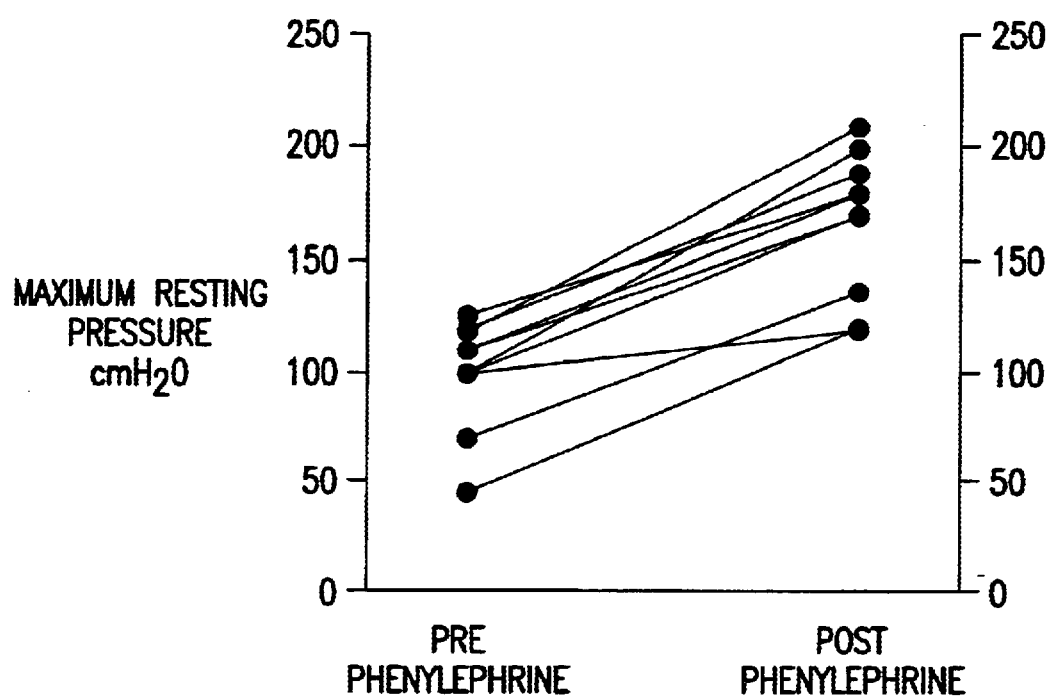
FIG. 1 represents a graph of maximum anal resting pressure after 0.5 ml of 10% phenylephrine (50 mg) applied intraanally in healthy volunteers.

Preparations of commercially available ophthalmic 10% phenylephrine hydrochloride (Minims) solution were administered intraanally with the subject in the left lateral position. The doses are expressed as both a volume of a concentration of phenylephrine solution and also as milligrams of phenylephrine. Before using ophthalmic phenylephrine solution intraanally, ointment preparations of phenylephrine made up in yellow soft paraffin were applied to the anal margin, but it was found this had no effect up to a dose of approximately 500 mg 10% ointment (50 mg of phenylephrine). This probably represents failure of transcutaneous absorption and thereafter only ophthalmic phenylephrine solution was instilled intraanally.

Manometry (to determine the maximum resting anal pressure) was performed using a water-filled microballoon system connected to a plastic rigid catheter and transducer and then to a pen chart recorder. Maximum resting anal pressure was obtained using a station pull through technique. The catheter was taped to the buttock and a continuous reading performed until a steady anal pressure was achieved. After the drug was administered, continuous pressure readings were taken for between 15 and 31 minutes. Pulse rate and blood pressure were monitored and the subject questioned for headache, anxiety, palpitations and abdominal or anal pain.

Dose Response Study in Single Volunteer

Ten percent phenylephrine was serially diluted with 0.9% saline and a standard 0.5 ml dose given to a single healthy volunteer. Commencing at it, increasing concentrations of phenylephrine were administered on different days until there was a rise in the resting anal pressure. To assess duration of action, in this one volunteer only, manometry was repeated at 13 hours.

There was no significant increase in the maximum resting pressure with 0.5 ml 0.1% (0.5 mg), 0.5% (2.5 mg), 1% (5 mg) or 5% (25 mg) phenylephrine. When 0.5 ml 10% phenylephrine (50 mg) was instilled into the anal canal, there was an increase in the resting pressure from 120 to 210 cm $H_2O$ (12–21 KPa). The increase in resting anal pressure was evident throughout 25 minutes of continuous recording but returned to pre-treatment level 13 hours later.

EXAMPLE 2

Healthy Volunteer Group

Ten healthy volunteers (five men) received an intraanal dose of the 0.5 ml 10% phenylephrine (50 mg) according to example 1. Median age was 26 years (range 22–37). None of the volunteers had symptoms of anal incontinence nor previous anal surgery and all the women were nulliparous and therefore presumed to have intact internal and external anal sphincters. Pre-phenylephrine median resting pressure was 110 cm $H_2O$ (11 KPa) (range 45–125 cm $H_2O$ ; 4.5–12.5 KPa).

After the application of 0.5 ml 10% phenylephrine (50 mg), there was a significant increase in the maximum resting pressure to 180 cm $H_2O$ (17.5 KPa) (range 120–210 cm $H_2O$ ; 12–20.5 KPa) (p<0.05, Wilcoxon sign rank test) (FIG. 1). The increased pressure was maintained for the duration of the recording, a median of 23 minutes (range 14–31 minutes).

EXAMPLE 3

A composition of base gel had the following composition: carmellose sodium 6 g, polyethylene glycol 30 ml, methylhydroxybenzoate 150 mg, propylhydroxybenzoate 15 mg, made up to volume with distilled water (pH 4).

Figure 2:
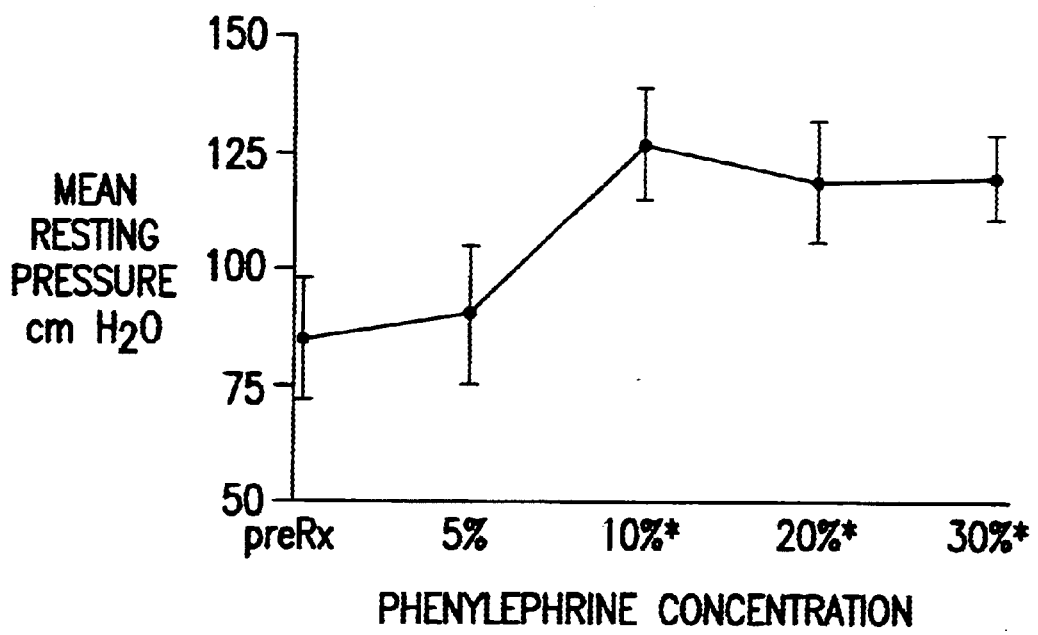
FIG. 2 represents a dose dependent graph of phenylephrine in healthy volunteers (prerx=Pre-treatment; MRP +/−1SD)

Various amounts of phenylephrine was added at 5%, 10%, 20% and 30% w/w to form various compositions for dose ranging studies (FIG. 2).

EXAMPLE 4

A base cream of the invention had the following composition:

| Dimethyl sulphoxide | 250 g |
| Carbomer 974P | 5 g |
| White soft paraffin | 15 g |
| Cetomacrogel emulsifying ointment* | 115 g |
| Propylene glycol | 23 g |
| Methylhydroxybenzoate (preservative soln) | to volume | to which 10% w/w phenylephrine hydrochloride was added.
composition: white soft paraffin 50 g, liquid paraffin 20 g, cetomacrogol emulsifying wax 30 g (cetosteryl alcohol 24 g and cetomacrogol 1000, 6 g).

A base cream was formed by firstly separate mixing of the aqueous and non-aqueous components of the cream. Weighed quantities of propylene glycol and a proportion of the preservative solution were placed in a beaker to which the weight quantity of carbomer powder was added using an impeller type mixer to form a colloidal suspension of the carbomer. Thereafter, the weighed quantity of DMSO was added and rapid stirring continued at room temperature until a translucent uniform gel had been formed.

In the meantime, the weighed quantities of white soft paraffin and the cetamacrogol emulsifying ointment were placed in a separate beaker, heated to melting point and gently stirred to give a uniform base.

The drug is then added to the remainder of the preservative solution, which in turn was then added to the gel and whilst vigorously stirring, the uniform base (above) was added to form a cream. The carbomer acting as a dual neutralisation agent and primary emulsifier (of the oil and aqueous phases) to form the uniform cream base.

EXAMPLE 5

Twelve human volunteers aged 21 to 53 (mean 35) were studied on 4 occasions. Measurements of resting anal sphincter pressure and anodermal blood flow (using a laser doppler flowmeter) were taken before and after topical application of increasing concentrations of phenylephrine gel according to example 3 (supplied by Slaco Pharma (UK) Ltd) to the anus. Readings were taken through the day after a single application in order to determine the duration of effect.

Figure 3:
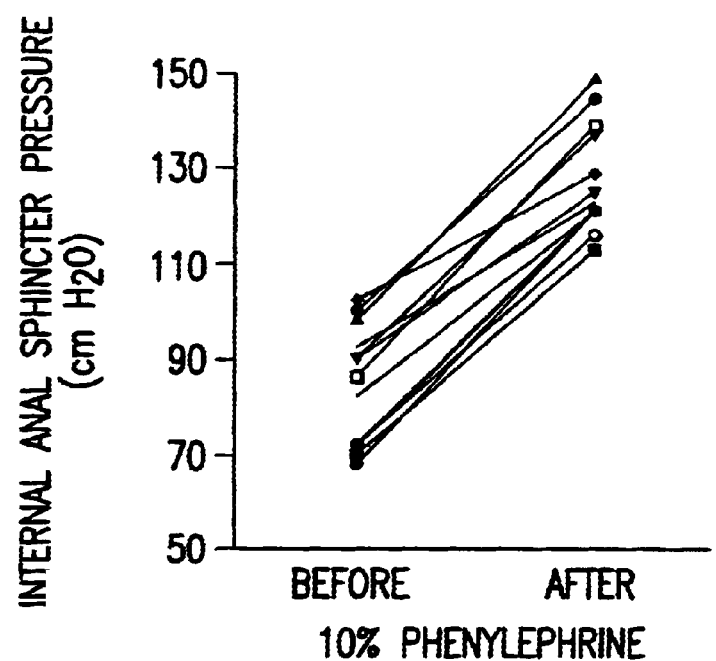
FIG. 3 represents a graph of maximum anal pressure in healthy volunteers before and after application of 10% phenylephrine.
Figure 4:
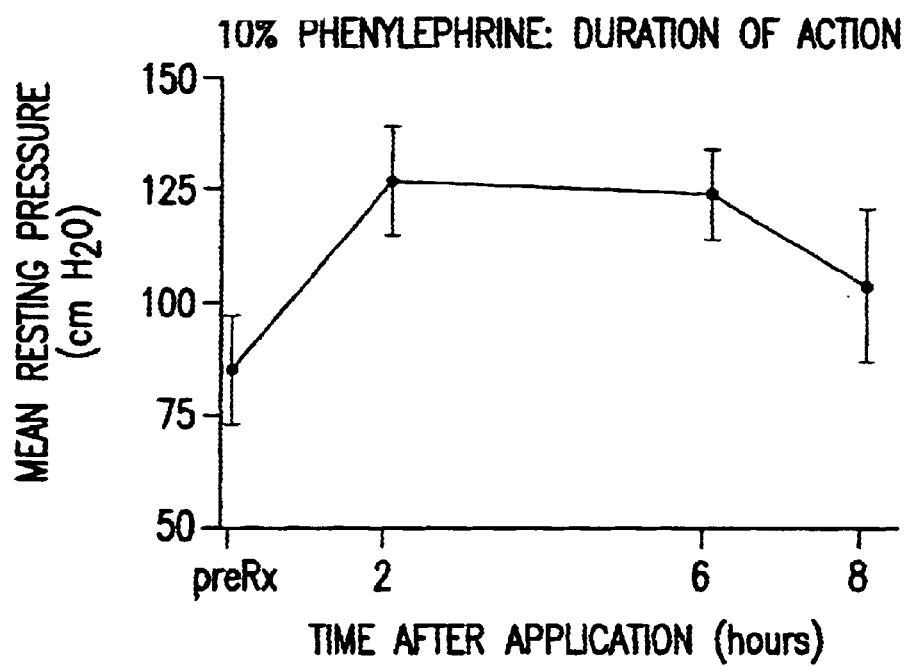
FIG. 4 represents a graph of the duration of action of 10% phenylephrine.

As can be seen from FIG. 2, there was a dose dependent increase in the mean resting anal sphincter pressure (MRP) with a small (6%) rise after 5% phenylephrine (p 0.04) and a clinically significant 33% rise with 10% phenylephrine compared to the pre-treatment sphincter pressure (85±12 v 127±12 cm$H_2O$ pre v post treatment MRP. P<0.0001)— FIG. 3. Thereafter no additional response was noted with higher concentrations of phenylephrine. Duration of action of a single application of 10% phenylephrine was a median of 7 (range 6 to 8) hours (FIG. 4). No notable changes were recorded in the anodermal blood flow. Therefore topical application of 10% phenylephrine gel significantly increases the resting anal sphincter pressure in healthy volunteers.

EXAMPLE 6

Patient Group

Ten patients (3 men) also received an intraanal dose of 0.5 ml 10% phenylephrine (50 mg) according to example 1. Their median age was 45 years (range 27–76). All had passive incontinence with or without urge faecal incontinence. Patients were selected on the basis of having passive faecal incontinence which is known to be associated with internal sphincter damage. To determine if the treatment is useful in those with structural fragmentation or simply thinning of the internal anal sphincter, five of each type of patient were collected.

Pre-phenylephrine median resting pressure was 25 cm $H_2O$ (2.5 KPa) (range 20–100 cm $H_2O$; 1–10 KPa). Endonanal ultrasound demonstrated an abnormal internal anal sphincter in all patients. In half the patients it was structurally fragmented while in the other five patients it was intact but abnormally thin (less than 1 mm). Seven patients also had some structural damage to the external anal sphincter, while in three it was circumferentially intact.

Figure 5:
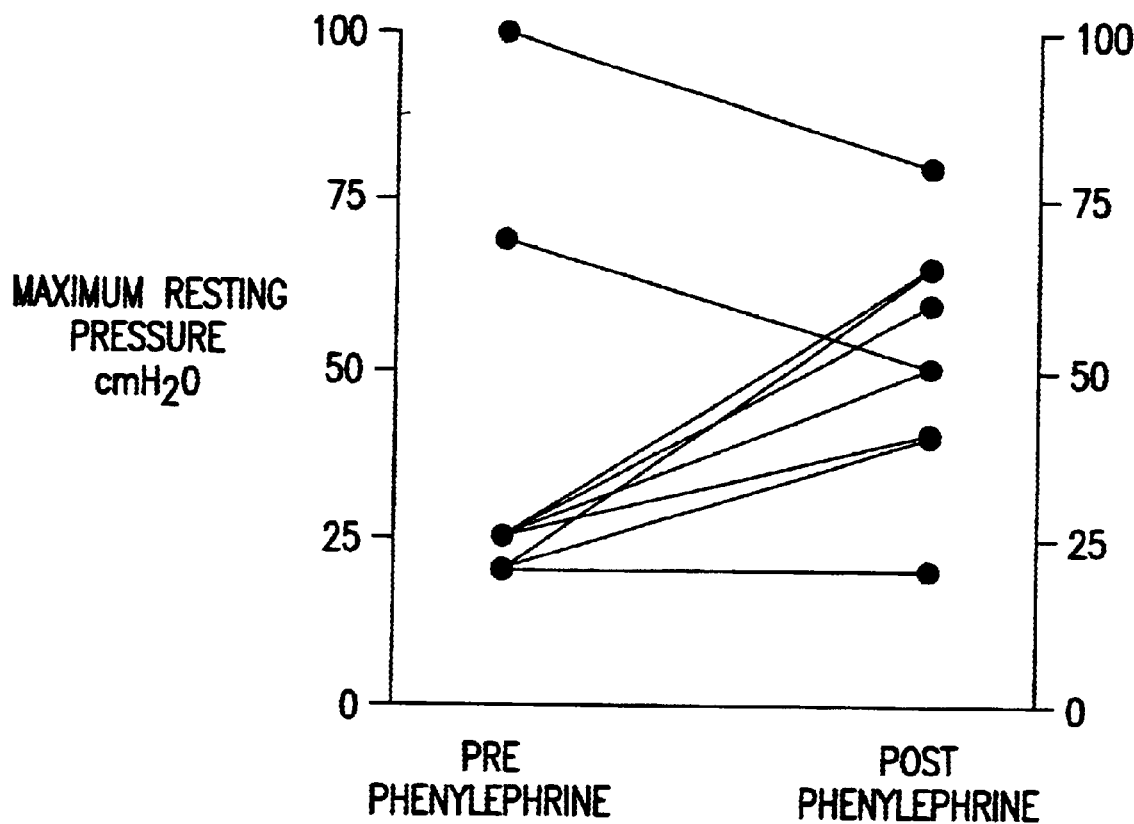
FIG. 5 represents a graph of maximum resting anal pressure after 0.5 ml of 10% phenylephrine (50 mg) applied intraanally in 10 patients with passive faecal incontinence.

After intraanal instillation of 0.5 ml 10% phenylephrine (50 mg) the median maximum resting pressure rose to 55 cm $H_2O$ (5.5 KPa) (range 20–80 cm $H_2O$; 2–8 KPa) (p=0.39, Wilcoxon sign rank test) (FIG. 5). Seven patients demonstrated a rise in anal pressure while two showed a fall and one patient showed no change. Increased resting pressure was seen in patients with both a fragmented, and a structurally intact, but thin, internal sphincter. The pre-treatment resting pressure did not predict the response to phenylephrine.

The pressure rise in incontinent patients although less consistent and not as marked as in healthy patients, is nevertheless surprising and therapeutically valuable in treating incontinence. The lower increase in resting anal pressure of incontinent patients can be explained in view of the known pathology of this condition. Patients with passive faecal incontinence have increased fibrosis and collagen replacement of the internal anal sphincter. Therefore although the absolute rise in resting anal pressure from phenylephrine was not as marked in responding patients compared with controls, it is nevertheless a major advance in the non-surgical treatment of passive faecal incontinence.

Although some patients did not respond to phenylephrine, this may be due to a structural abnormality or to an altered sensitivity of their internal anal sphincter. These patients will probably require an increased dose (over the 50 mg tested in this study) to produce a rise in their resting anal pressure.

EXAMPLE 7

A prospective randomised placebo controlled cross over trial was undertaken to evaluate the use of 10% phenylephrine topical cream (according to examples 3 and 4) for treatment of idiopathic passive fecal incontinence.

30 Patients completed the study. All patients were assessed by endoanal ultrasound as well as anorectal physiology (to determine maximum resting anal pressure) and laser doppler flowmetry prior to treatment. The latter two measurements are repeated after a 3 week trial of the active agent (phenylephrine 10%) and placebo 'Incontinence scores' are determined before and after each treatment.

Of the 30 patients studied, three (10%) had significant subjective improvements of their symptoms after phenylephrine compared to the pre-treatment baseline, and to placebo. All three were women, aged 55 to 64 (mean 59), who had low/normal resting sphincter pressure prior to treatment and structurally intact anal sphincter on ultrasound. Anorectal manometry showed no significant change in mean resting pressure after 10% phenylephrine (from 62 to 58 $cmH_2O$, pre and post phenylephrine). Similarly no significant change in pressure was noted after placebo. Incontinence score improved from mean of 14 to mean of 10. There was no significant change in anodermal blood flow after phenylephrine or placebo.

In summary 3/30 patients with idiopathic fecal incontinence had subjective improvement of their symptoms after topical application of 10% phenylephrine cream, with noticeable improvement in their incontinence score.

EXAMPLE 8

A prospective randomised placebo controlled cross over trial was undertaken to evaluate the use of phenylephrine 10% topical cream (according to examples 2a and 3) for treatment of fecal incontinence in patients with ileo-anal pouch.

12 Patients were enrolled in the study of whom 10 have completed the study. 10 Patients are mainly troubled by nocturnal incontinence only, and 2 have both daytime and nocturnal incontinence.

Of the 10 completed studies, there were 7 women and 3 men, age range (34–67). Anorectal manometry was performed and laser doppler fowmetry on all patients. Incontinence score was determined. All these outcome measures were repeated after treatment with both trial creams (phenylephrine and placebo).

6/10 (60%) patients had significant improvement of their symptoms with phenylephrine 10% compared to placebo. This correlated well with the rise in mean resting anal sphincter pressure in these patients after phenylephrine but not after placebo (29% increased after phenylephrine, v-8% on placebo compared to baseline, p<0.005). Incontinence scores improved by a mean of 45% after phenylephrine compared to 3% after placebo. No differences in anodermal blood flow were noted. The mean subjective improvement in symptoms reported by patients was 83% after placebo and 14% after placebo (p<0.01).

One patient had no measurable increase in anal sphincter pressure, though her incontinence score improved by 47% and subjectively she felt 75% better after phenylephrine compared to placebo. 3/10 patients had no improvement.

In summary, 7/10 patients with ileo-anal pouch had improvement of symptoms of incontinence after topical application of 10% phenylephrine cream, 6 of whom also had objective improvement i.e. measurement of anal sphincter pressure.

EXAMPLE 9

A 1% ointment was prepared by mixing 0.02 g of Nω—Nitro-L-arginine (obtained from Fluka—part of the Sigma group) in 19.8 g of unguentum merk base.

The ointment was then applied in and around the anal canal of twelve patients and the internal anal pressure measured by manometry (as discussed previously) before and shortly after application of the ointment. The patients suffered from passive and urge (P+U) incontinence, or constipation, and ultra-sound showed most patients to have an internal anal sphincter (IAS) and external anal sphincter (EAS) defect.

The results are given in Table 1 and show that nitric oxide synthase inhibitors such as NωNitro-L-arginine increase the resting internal anl sphincter pressure and relieve anal incontinence and anal itch.

TABLE 1

| | Patient age/sex | | Diagnosis | Anal Ultra-sound | Internal Anal Pressure/Pre Application | Post Application |
|---|---|---|---|---|---|---|
| 1 | 24 | M | P + U Incont. | IAS & EAS Defect | 80 | 100 |
| 2 | 81 | M | P + U Incont. | IAS & EAS Defect | 40 | 50 |
| 3 | 97 | M | P + U Incont. | IAS & EAS Intact | 80 | 100 |
| 4 | 24 | F | Constipation | | 80 | 100 |
| 5 | 37 | F | Constipation | | 80 | 100 |
| 6 | 38 | F | Constipation | | 60 | 80 |
| 7 | 37 | M | P + U Incont. | s/p Sphinctorectomy IAS & EAS Defect | 40 | 50 |

TABLE 1-continued

| | Patient age/sex | | Diagnosis | Anal Ultra-sound | Internal Anal Pressure/Pre Application | Post Application |
|---|---|---|---|---|---|---|
| 8 | 37 | F | Constipation | IAS & EAS intact | 80 | 100 |
| 9 | 73 | M | P + U Incont. | IAS & EAS Intact | 60 | 60 |
| 10 | 55 | F | P + U Incont. | IAS & EAS Intact | 40 | 60 |
| 11 | 60 | F | P + U Incont. | IAS & EAS Defect | 30 | 40 |
| 12 | | M | P + U Incont. Viserol Myopathy | IAS & EAS Intact | 30 | 30 |

What is claimed is:

1. A method for the treatment of fecal incontinence comprising topically administering in and/or around the anal canal of a patient, a topical composition comprising 5% w/w to 50% w/w of phenylephrine or a pharmacologically acceptable salt thereof in an amount effective to increase the internal anal sphincter pressure.

2. A method for the treatment of fecal incontinence according to claim 1 comprising topically administering in and/or around the anal canal of a patient, a topical composition comprising as the sole physiologically active agent a fecal incontinence treating amount of phenylephriie or a pharmacologically acceptable salt thereof.

3. The method according to claim 1, wherein the topical composition comprises at least 10% w/w phenylephrine.

4. A method for the treatment of fecal incontinence according to claim 1 or claim 3 comprising topically administering in and/or around the anal canal of a patient, a topical composition comprising as the sole physiologically active agent phenylephrine or a pharmacologically acceptable salt thereof.

5. The method according to claim 1, 2, or 3, wherein the patient to be treated has a normal or low maximum anal resting pressure and a structurally intact internal anal sphincter muscle.

6. The method according to claim 1, 2, or 3, wherein the patient to be treated has had major bowel resection and reanastomosis.

7. The method according to claim 1, 2, or 3, wherein the active agent is applied locally to the internal anal sphincter.

* * * * *